United States Patent
Olson et al.

(10) Patent No.: US 8,077,310 B2
(45) Date of Patent: Dec. 13, 2011

(54) SYSTEM AND METHOD OF CAPTURING MULTIPLE SOURCE EXCITATIONS FROM A SINGLE LOCATION ON A FLOW CHANNEL

(75) Inventors: David C. Olson, Ann Arbor, MI (US); Collin A. Rich, Ypsilanti, MI (US)

(73) Assignee: Accuri Cytometers, Inc., Ann Arbor, MI (US)

( * ) Notice: Subject to any disclaimer, the term of this patent is extended or adjusted under 35 U.S.C. 154(b) by 567 days.

(21) Appl. No.: 11/848,229

(22) Filed: Aug. 30, 2007

(65) Prior Publication Data

US 2008/0055595 A1 Mar. 6, 2008

Related U.S. Application Data

(60) Provisional application No. 60/894,837, filed on Mar. 14, 2007, provisional application No. 60/823,947, filed on Aug. 30, 2006.

(51) Int. Cl.
*G01J 3/30* (2006.01)
(52) U.S. Cl. ..................................................... 356/318
(58) Field of Classification Search .................. 356/318, 356/417; 250/458.1–461.2
See application file for complete search history.

(56) References Cited

U.S. PATENT DOCUMENTS

| | | |
|---|---|---|
| 4,691,829 A | 9/1987 | Auer |
| 4,755,021 A | 7/1988 | Dyott |
| 5,150,313 A | 9/1992 | van den Engh et al. |
| 5,204,884 A | 4/1993 | Leary et al. |
| 5,224,058 A | 6/1993 | Mickaels et al. |
| 5,270,548 A | 12/1993 | Steinkamp |
| 5,308,990 A | 5/1994 | Takahashi et al. |
| 5,367,474 A | 11/1994 | Auer |
| 5,469,375 A | 11/1995 | Kosaka |
| 5,684,480 A | 11/1997 | Jansson |
| 5,883,378 A | 3/1999 | Irish |
| 5,981,180 A | 11/1999 | Chandler |
| 6,108,463 A | 8/2000 | Herron et al. |
| 6,115,065 A | 9/2000 | Yadid-Pecht et al. |
| 6,139,800 A * | 10/2000 | Chandler .................. 422/82.08 |
| 6,181,319 B1 | 1/2001 | Fujita |
| 6,710,871 B1 | 3/2004 | Goix |
| 6,778,910 B1 | 8/2004 | Vidal |
| 6,809,804 B1 | 10/2004 | Yount |
| 6,816,257 B2 | 11/2004 | Goix |
| 6,890,487 B1 | 5/2005 | Sklar et al. |
| 6,897,954 B2 | 5/2005 | Bishop |
| 7,019,834 B2 | 3/2006 | Sebok |
| 7,024,316 B1 | 4/2006 | Ellison |

(Continued)

FOREIGN PATENT DOCUMENTS

JP 356169978 A 12/1981

(Continued)

*Primary Examiner* — Tarifur Chowdhury
*Assistant Examiner* — Abdullahi Nur
(74) *Attorney, Agent, or Firm* — Jeffrey Schox

(57) ABSTRACT

The invention includes a system and a method for capturing multi source excitations from a single location on a flow channel. The system preferably includes a light subsystem that emits light onto a single location on a flow channel, a detector subsystem to detect light emitted from the single location on the flow channel, and a processor to separate the detected light. The method preferably includes emitting light onto a single location on a flow channel, detecting light emitted from the single location on the flow channel, and separating the detected light.

18 Claims, 5 Drawing Sheets

U.S. PATENT DOCUMENTS

| | | |
|---|---|---|
| 7,106,442 B2 | 9/2006 | Silcott et al. |
| 7,130,046 B2 | 10/2006 | Fritz |
| 7,274,316 B2 | 9/2007 | Moore |
| 7,362,432 B2 | 4/2008 | Roth |
| 2002/0028434 A1 | 3/2002 | Goix et al. |
| 2002/0080341 A1 | 6/2002 | Kosaka |
| 2003/0035168 A1* | 2/2003 | Qian et al. ............ 359/124 |
| 2003/0054558 A1 | 3/2003 | Kurabayashi |
| 2003/0078703 A1 | 4/2003 | Potts et al. |
| 2003/0223061 A1 | 12/2003 | Sebok |
| 2004/0131322 A1 | 7/2004 | Ye et al. |
| 2004/0143423 A1 | 7/2004 | Parks et al. |
| 2004/0246476 A1* | 12/2004 | Bevis et al. ............ 356/237.5 |
| 2005/0073686 A1 | 4/2005 | Roth et al. |
| 2006/0015291 A1 | 1/2006 | Parks et al. |
| 2006/0219873 A1 | 10/2006 | Martin et al. |
| 2007/0124089 A1 | 5/2007 | Jochum |
| 2008/0228444 A1 | 9/2008 | Olson et al. |
| 2010/0012853 A1 | 1/2010 | Parks |
| 2010/0032584 A1 | 2/2010 | Dayong et al. |

FOREIGN PATENT DOCUMENTS

| | | |
|---|---|---|
| JP | 356169978 A | 12/1981 |
| WO | 2005017499 | 2/2005 |
| WO | 2005068971 | 7/2005 |
| WO | WO/2005/068971 | 7/2005 |
| WO | 2005091893 | 10/2005 |
| WO | WO/2005/091893 | 10/2005 |
| WO | WO/2006/055722 | 5/2006 |
| WO | 2007/103969 | 3/2007 |
| WO | 2010/101623 | 9/2010 |

* cited by examiner

SYSTEM AND METHOD OF CAPTURING MULTIPLE SOURCE EXCITATIONS FROM A SINGLE LOCATION ON A FLOW CHANNEL

CROSS-REFERENCE TO RELATED APPLICATIONS

This application claims the benefit of U.S. Provisional Application No. 60/823,947, filed 30 Aug. 2006, and U.S. Provisional Application No. 60/894,837, filed 14 Mar. 2007, which are incorporated in their entirety by this reference.

TECHNICAL FIELD

This invention relates generally to the flow cytometry field, and more specifically to a new and useful system and method of capturing multiple source excitations in the flow cytometry field.

BACKGROUND

This application is related to U.S. Pat. No. 5,909,278, issued Jun. 1, 1999, which is incorporated in its entirety by this reference.

As shown in FIG. 1, the traditional multi-source excitation detection system is a fixed, inflexible design that uses four Photo-Multiplier Tubes (PMT) to detect a maximum of four fluors, resulting in one fluor detected per PMT. A fluor is a small molecule, or a part of a larger molecule, which absorbs light and, in the case of a fluorophore, emits light through fluorescence. Dyes containing fluors with similar emission spectra can be used together if they are excited by different lasers. The excitation sources and detectors are typically spaced 200 microns apart, and the excitation sources are permanently assigned to be a 488 nm laser or a 633 nm laser.

As shown in FIG. 2, other traditional multi-source excitation detection systems, which have a slightly more flexible design, use four Photo-Multiplier Tubes (PMT) to detect a maximum of four Fluors, still resulting in one Fluor detected per PMT. This system features coincident lasers and detectors, where the detectors are permanently assigned to both 488 nm and 633 nm laser beams, but cannot distinguish between the results of them. Dyes with similar emission spectra cannot be used together, even if the dyes are excited by different lasers. The system shown in FIG. 2 features improved flexibility over the system shown in FIG. 1, but the detection is limited to four non-overlapping fluorophores.

With the traditional systems shown in FIGS. 1-2, adding additional analytical capability (the ability to detect additional colors) requires addition of detectors, which increases cost, complexity, and size. Presently in the art, a single detector system cannot distinguish between two or more fluorphores when excited by two or more excitation sources and when having overlapping fluoresecence.

Thus, there is a need in the flow cytometer field to create a new and useful multi-source excitation detection system. This invention provides such new and useful multi-source excitation detection system.

SUMMARY OF THE INVENTION

The present invention allows single detector subsystem (which may include a single detector) to distinguish between two or more fluorophores when excited by two or more excitation sources and when having overlapping fluorescence, and to achieve measurements of more than one fluor per detector. One potential advantage of the invention is that it expands the analytical capability of an instrument without requiring additional detectors, reducing cost and saving space. Another potential advantage of the invention is that it increases the utility of the available detectors, resulting in greater overall analytical capability without the need to add additional detectors. Another potential advantage of the invention is that it expands the usable selection of fluorophores to fluorophores whose emissions populate a wide spectrum of visible light.

The invention enables independent detection of multiple fluorophores, possibly with overlapping fluorescence spectra, emitted from one location in the flow channel, using a single detector subsystem, when the fluorophores at one location in the flow channel each respond substantially and/or uniquely to one of multiple excitation source modes used for excitation.

DESCRIPTION OF THE PREFERRED EMBODIMENTS

Figure 1:
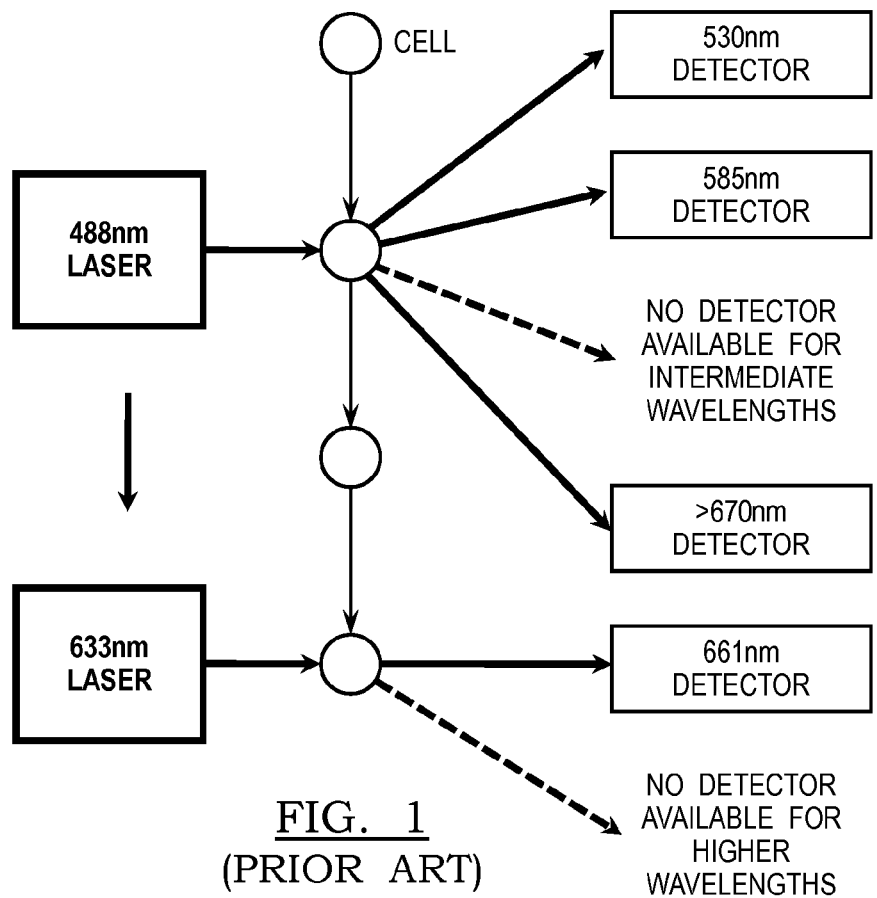
FIGS. 1 and 2 are conceptual diagrams of systems in the prior art.
Figure 2:
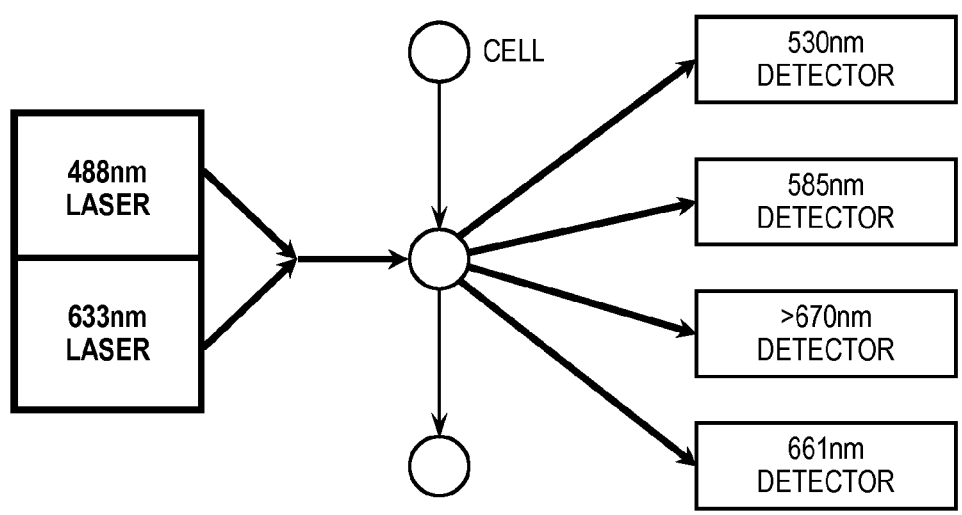
Figure 3:
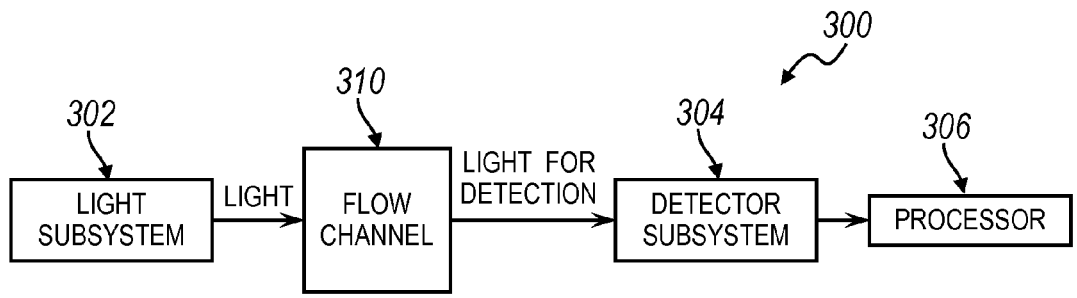
FIG. 3 is a schematic representation of a first preferred embodiment of the invention.
Figure 4:
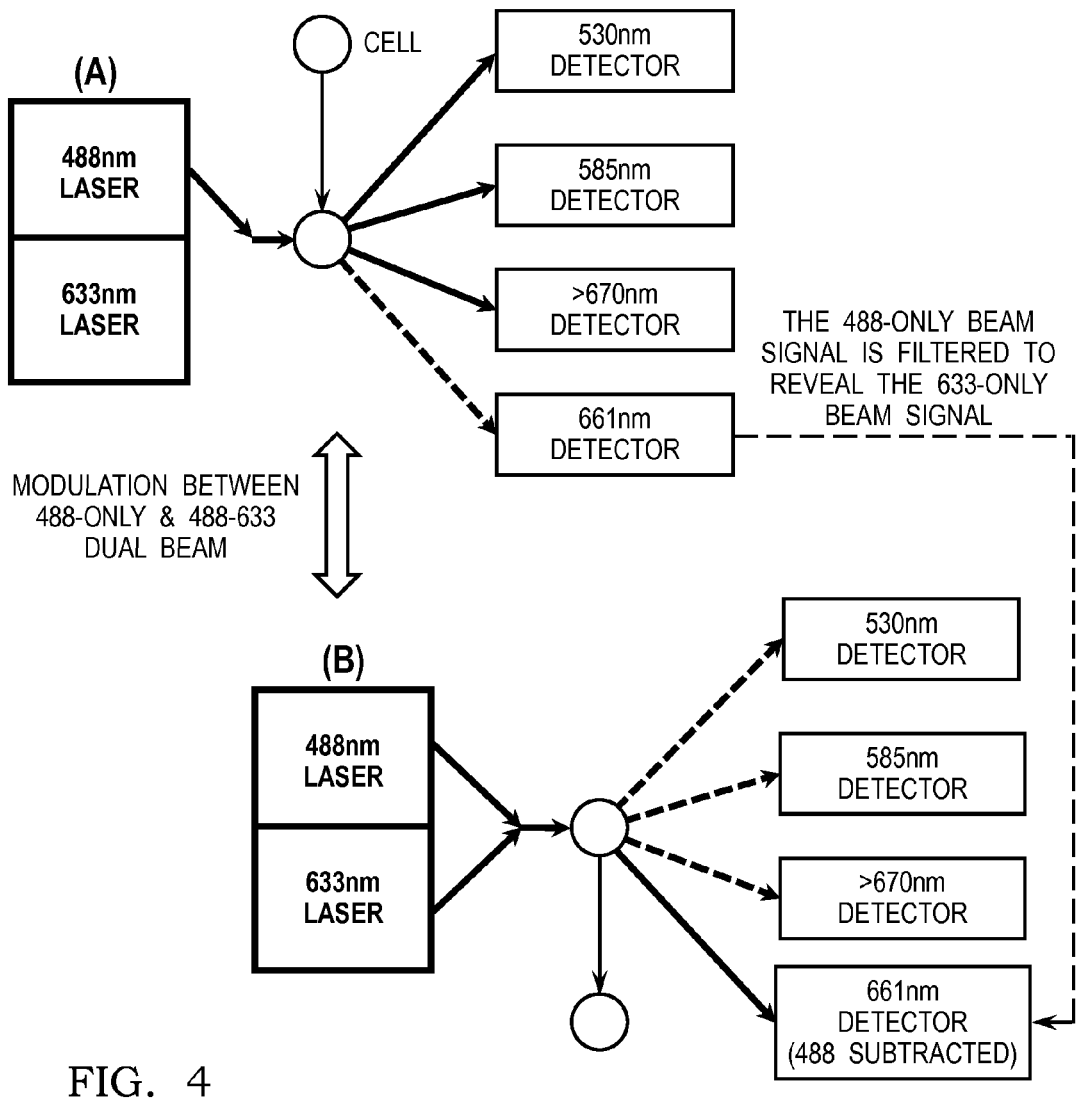
FIG. 4 is a conceptual diagram of a first variation of the first preferred embodiment of the invention.
Figure 5:
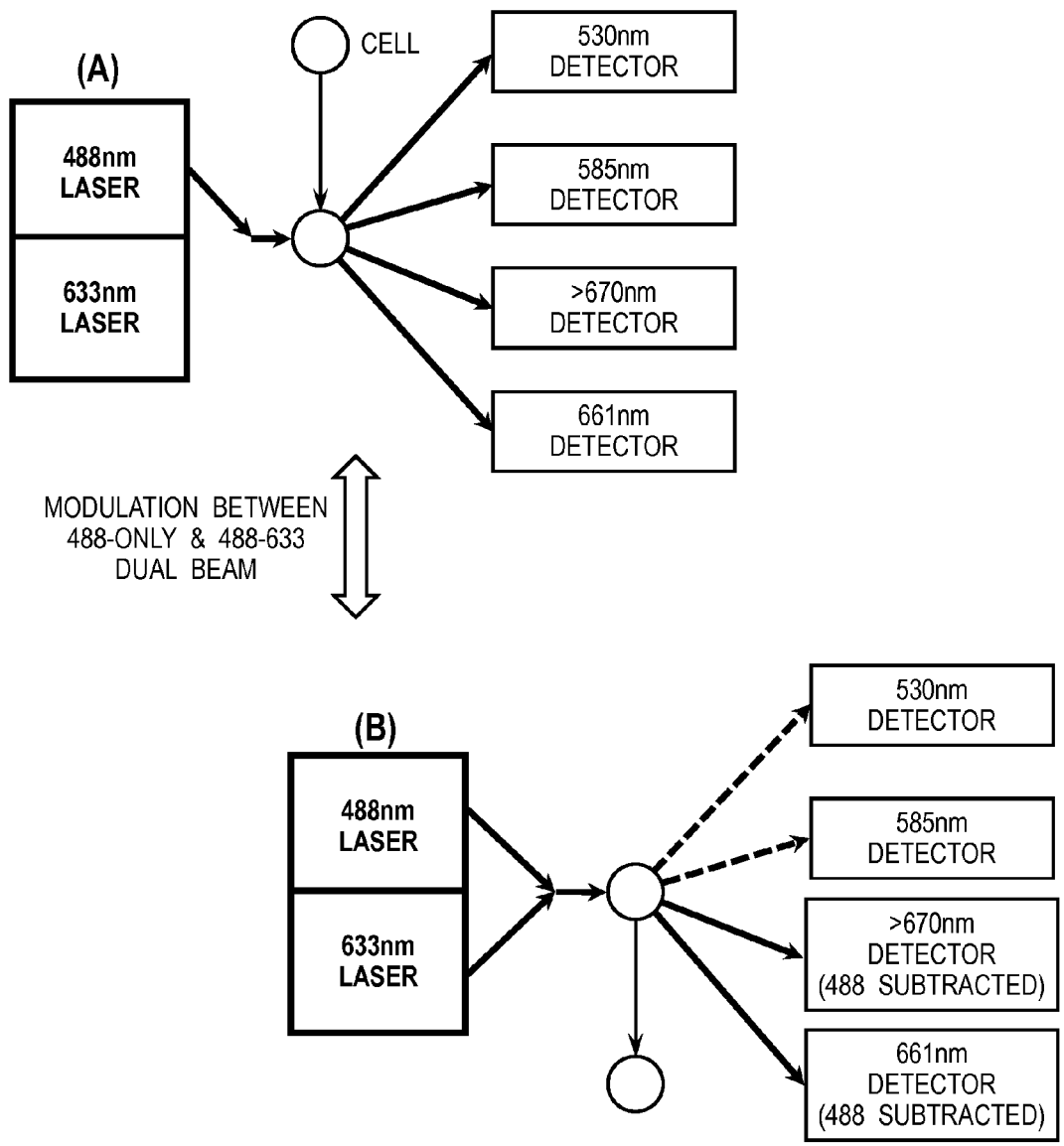
FIG. 5 is a conceptual diagram of a second variation of the first preferred embodiment of the invention.
Figure 6:
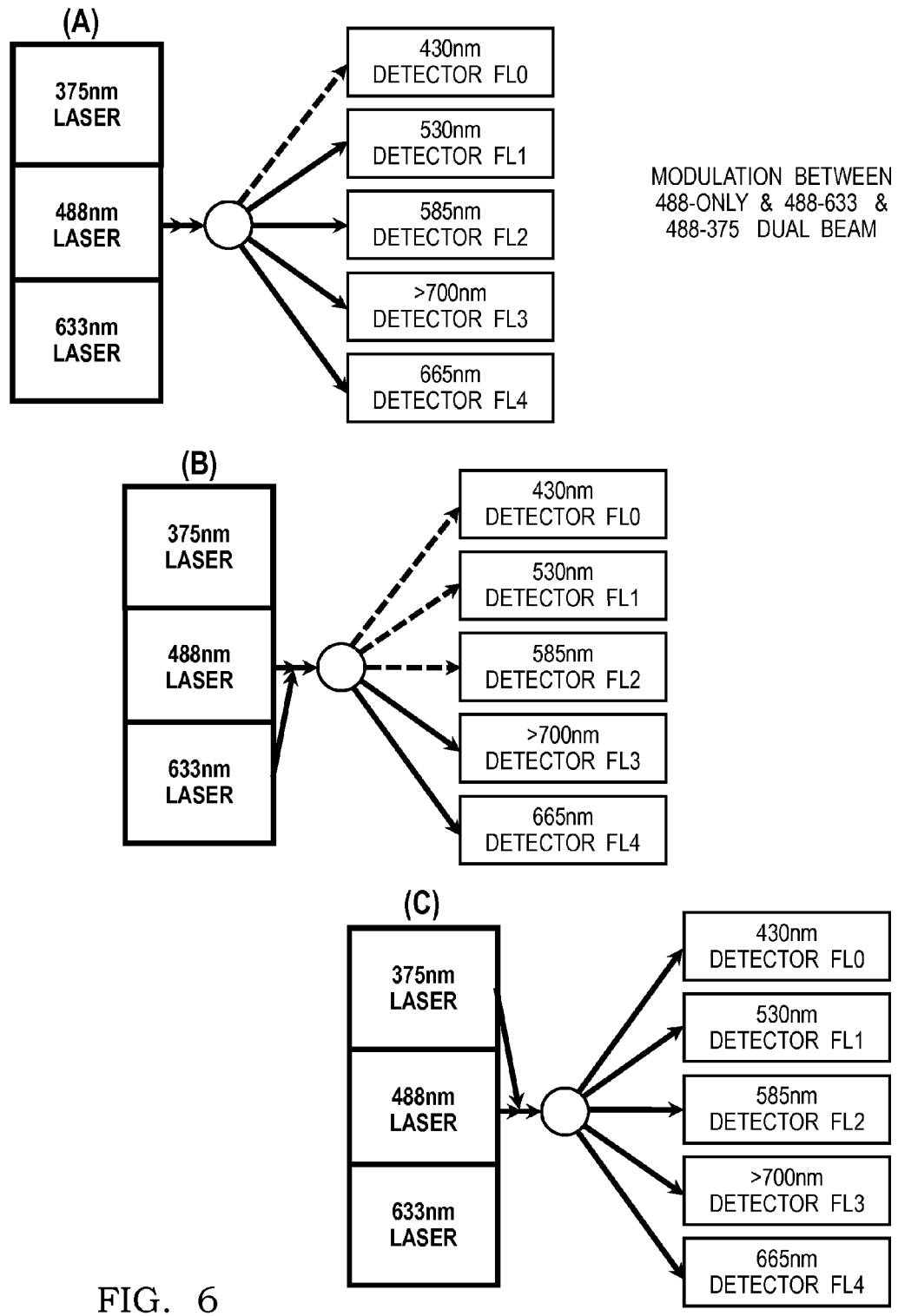
FIG. 6 is a conceptual diagram of a third variation of the first preferred embodiment of the invention.
Figure 7:
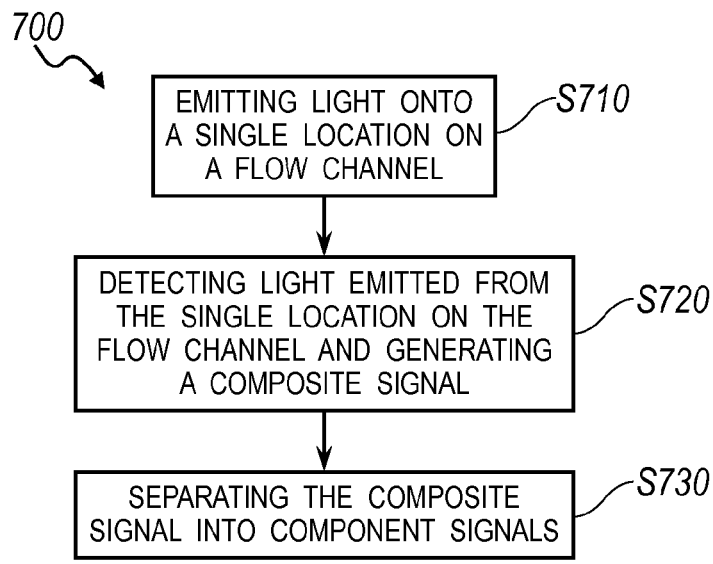
FIG. 7 is a flowchart representation of a second preferred embodiment of the invention.

The following description of the preferred embodiments of the invention is not intended to limit the invention to these preferred embodiments, but rather to enable any person skilled in the art to make and use this invention. The preferred embodiment of a system for capturing multiple excitations from a single location on a flow channel is shown in FIG. 3. Conceptual diagrams of three preferred variations of the preferred system are shown in FIGS. 4-6. A method for capturing multiple excitations from a single location on a flow channel is shown in FIG. 7.

As shown in FIG. 3, the system 300 preferably includes a light subsystem 302 that emits light onto a single location of a flow channel 310, a detector subsystem 304 that detects emitted light from the single location on the flow channel 310, and a processor 306.

The light subsystem 302 functions to emit light onto a single location on a flow channel 310. This single location on the flow channel 310 may also be referred to as the interrogation zone. Preferably, at least two excitation sources are used. The excitation sources are preferably lasers of different wavelengths, and even more preferably are lasers of wavelengths 488 nm, 375 nm, and 633 nm. The excitation sources are preferably operated in at least one excitation source operating mode. The emitted light from any and all excitation sources in any and all excitation source operating modes is preferably emitted onto a single location on the flow channel. The light subsystem also preferably includes some form of modulation between at least two operating modes. Preferably time domain multiplexing is used, but any type of modulation or multiplexing could be used, such as frequency division multiplexing or code division multiplexing. The light subsystem may include any number of any type of exciter (such as lasers, or LEDs) at any wavelength and/or using any modulation technique. Preferably, at least one target (such as a cell) is in the flow channel 310, and is preferably labeled with at least one of two or more fluorophores, where one of the fluorphores is excited by wavelength A and the other fluorophore by wavelength B, however, any number of fluorophores may be excited by any number of wavelengths. For a cytometer with n>1 excitation source modes in the light subsystem 302, the system 300 preferably modulates at least (n−1) excitation source modes independently in the light subsystem 302.

In a first and a second preferred variation, shown in FIGS. 4-5, respectively, the light subsystem 302 includes a 488 nm laser and a 633 nm laser, operating in two excitation source operating modes: 1) where only the 488 nm laser is emitting light onto a single location on the flow channel, and 2) where both the 488 nm laser and the 633 nm laser are emitting light onto a single location on the flow channel. The light subsystem 302 preferably modulates the two excitation source operating modes, more preferably one excitation source operating mode is modulated at 1.25 MHz and another excitation source operating source mode is modulated at 5 MHz. However, the modulation may be done at any frequency, provided that the modulaton satisfies the Nyquist criteria for the bandwidth of the pulse envelope of the excitation source operating modes.

In a third preferred variation, shown in FIG. 6, the light subsystem includes a 488 nm laser, a 633 nm laser, and a 375 nm laser operating in three excitation source operating modes: 1) where only the 488 nm laser is emitting light onto a single location on the flow channel, 2) where both the 488 nm laser and the 633 nm laser are emitting light onto a single location on the flow channel, and 3) where both the 488 nm laser and the 375 nm laser are emitting light onto a single location on the flow channel. The light subsystem 302 preferably modulates the three excitation source operating modes, more preferably at least one excitation source operating mode is modulated at 1.25 MHz and another excitation source operating source mode is modulated at 5 MHz. However, the modulation may be done at any frequency, provided that the modulaton satisfies the Nyquist criteria for the bandwidth of the pulse envelope of the excitation source operating modes.

The detector subsystem 304 functions to detect light emitted from one location on the flow channel 310 (or, more specifically, the interrogation zone of the flow channel 310). The detector subsystem 304 preferably detects fluorescent light emitted from objects in the single location on flow channel that have been excited by the emitted light from the light subsystem 302, however, the detector subsystem 304 may detect any type of light from any source. The detector subsystem 304 preferably includes one or more detectors in a spatial arrangement around a single location on the flow channel or alternatively, another spatial location in the interrogation zone. As shown in a first and second preferred variations in FIGS. 4-5 the detector subsystem preferably includes at least four detectors. The four detectors are preferably able to detect light of at least one of the following wavelengths: 530 nm, 585 nm, 661 nm, and wavelengths greater than 670 nm. As shown in a third preferred variation in FIG. 6, the detector subsystem preferably includes at least five detectors. The five detectors are preferably able to detect light of at least one of the following wavelengths: 430 nm, 530 nm, 585 nm, 665 nm, and wavelengths greater than 700 nm. The detector subsystem is preferably at least one photomultiplier tube, but may alternatively be any suitable detector. The detector subsystem 304 outputs a composite signal of the detected light emitted from a single location on the flow channel for the current excitation source operating mode of the light subsystem 302.

Figure 8:
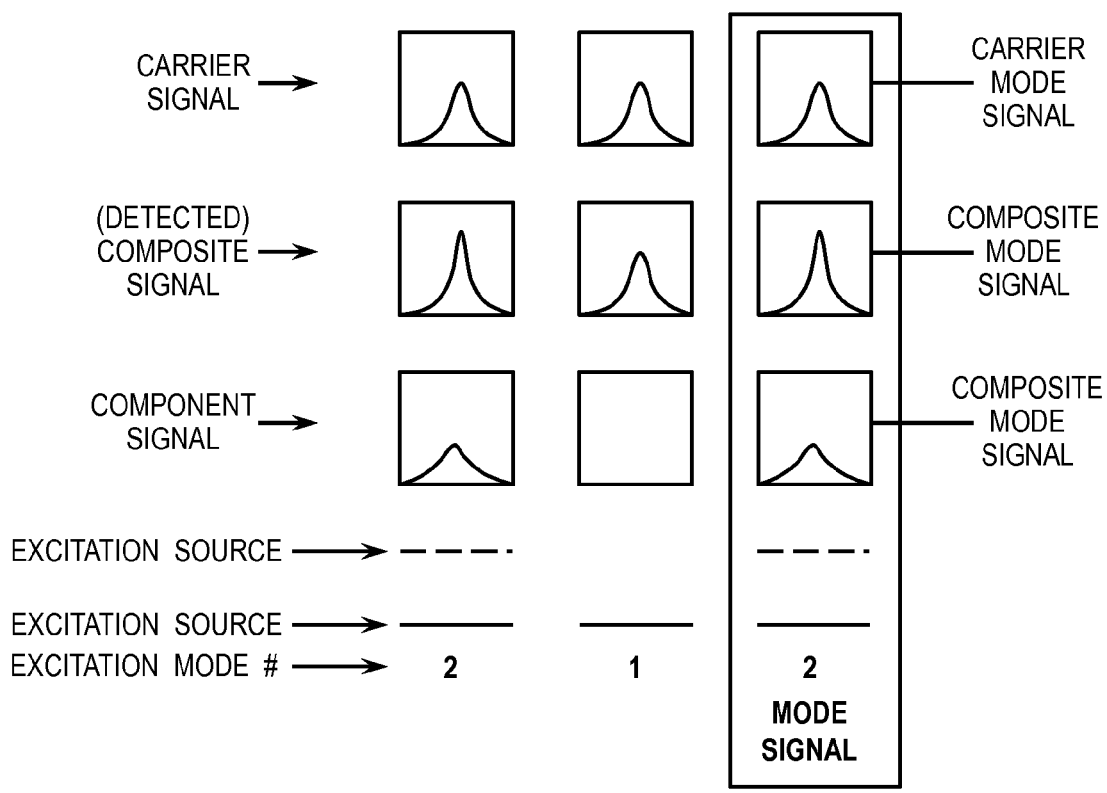
FIG. 8 is a schematic representation of the signal processing operations performed by the processor of the preferred embodiment.

As shown in FIG. 8, the processor 306 functions to separate the composite signal from the detector subsystem 304 into composite mode signals corresponding to each excitation source operating mode and the signals are preferably analyzed separately. The processor 306 preferably derives at least one additional component signal from the first composite mode signal corresponding to the first excitation source operating mode and the second composite mode signal corresponding to the second excitation source operating mode. The processor 306 is preferably included in the electronics system for a flow cytometer (or other instrumentation that uses fluorescence-based detection). The composite signal from the detector subsystem 304 may be fed to a single processor 306 or multiple processors. Preferably, for a cytometer with more than one independently modulated excitation source mode from the light subsystem 302, the processor 306 synchronously demodulates the correspondingly modulated composite signal. As shown in a first variation in FIG. 4, the processor 306 may be used to derive additional component signals by subtracting, separating, filtering or otherwise distinguishing the component mode signal corresponding to a first excitation source operating mode, from the component mode signal corresponding to a second excitation source operating mode. As shown in a second variation in FIG. 5, the processor 306 may independently measure and/or process the component mode signal corresponding to each excitation source operating mode, thus detecting multiple component signals per PMT (6 Fluors for 4 PMTs, or 1.5 Fluors per PMT in this case). As shown in FIG. 6, the processor 306 may be used to derive (by subtracting, separating, filtering or otherwise distinguishing) additional component mode signals from the composite mode signals corresponding to each excitation source operating mode, and thus detect even more component mode signals per PMT, (11 Fluors for 5 PMTs or 2.2 Fluors per PMT in this example).

As an example, using the first preferred embodiment of the invention, it is possible to record the individual fluorescence signatures generated by two 488 nm excited fluorophores and two 633 nm excited fluorophores (for total of four fluorophores) simultaneously with just two detectors in the detector subsystem. The processor allows for differentiating two component mode signals from within a composite signal even when one component mode signal is much larger than the other. If the 488 nm component mode signal is a value of 1,000,000, and the 633 nm component mode signal is a value of 10, the red plus blue composite mode signal is 1,000,010. The low error rate makes it possible to subtract the blue component mode signal (1,000,000) from the composite mode signal (1,000,010) and still capture and analyze the remaining component mode signal (10).

The first preferred embodiment of the invention may be used with any system that includes at least one exciter in a light subsystem 302, at least one detector in a detector subsystem 304, and at least one processor 306, in an electronics system, such as a flow cytometer, a fluorescence microscope, a fluorimeter and a fluorescence plate reader (also known as a well plate or microtiter plate reader).

As shown in FIG. 7, a method 700 for capturing multiple source excitations from a single location on a flow channel includes emitting light onto a single location on a flow channel S710, detecting light emitted from the single location on the flow channel and generating a composite signal S720, and separating the composite signal into component signals S730.

Step S710 functions to emit light onto a single location on a flow channel. This light is preferably emitted from at least two excitation sources, with each source preferably at different wavelengths. In a first variation, S710 preferably includes operating the excitation sources in at least one of the following excitation source operating modes: 1) emitting light onto the single location on the flow channel from only one excitation source, and 2) emitting light onto the single location on the flow channel from a first excitation source and a second excitation source. In a second variation, S710 preferably further includes emitting light from three excitation sources, where the third excitation source wavelength is preferably different from the first and second excitation source wavelengths and operating the excitation sources in at least one of the following additional excitation source operating modes: 1) emitting onto the single location on the flow channel from only the first excitation source and third excitation source, 2) emitting onto the single location on the flow channel from only the second excitation source and third excitation source, and 3) emitting onto the single location on the flow channel from the first excitation source, the second excitation source, and third excitation source. In both the first and second preferred variations of S710, the excitation source operating modes are preferably separated by modulation, if multiple excitation source operating modes are used, more preferably time domain multiplexing is used, but any type of modulation or multiplexing could be used, such as frequency division multiplexing or code division multiplexing. The excitation source operating modes are preferably modulated, more preferably, in the case of two excitation source operating modes, one operating mode is modulated at 1.25 MHz and another operating source mode is modulated at 5 MHz. However, the modulation may be done at any frequency, provided that the modulation satisfies the Nyquist criteria for the bandwidth of the pulse envelope of the excitation source operating modes.

Step S720 functions to detect light emitted from the single location on the flow channel and generate a composite signal. The output of all detected light during one excitation source operating mode is preferably included in the composite signal. The detected light is preferably fluorescent light emitted from a single location on the flow channel that has been excited by light emitted during an excitation source operating mode, but the detected light may be of any wavelength, and be from any source.

Step S730 functions to separate the composite signal into component signals. S730 preferably further includes separating the composite signal into composite mode signals corresponding to each excitation source operating mode. More preferably, S730 includes demodulating the separated composite mode signals by deriving at least one component mode signal from the separated composite mode signals corresponding to at least two respective excitation source operating modes. More preferably still, the deriving of at least one component mode signal from the separated composite mode signals corresponding to at least two respective excitation source operating modes, further includes subtracting, separating, filtering or distinguishing the composite mode signals.

As a person skilled in the art will recognize from the previous detailed description and from the figures and claims, modifications and changes can be made to the preferred embodiments of the invention without departing from the scope of this invention defined in the following claims.

We claim:

1. A system for capturing multi source excitations from a single location on a flow channel comprising:
   a light subsystem that emits light onto a single location on a flow channel, wherein the light subsystem includes a first excitation source that emits light at a first wavelength and a second excitation source that emits light at a second wavelength that is different from the first wavelength, wherein the light subsystem modulates between the following excitation source operating modes:
      a first excitation source operating mode, wherein only one of the first and second excitation sources emits light onto the single location on the flow channel; and
      a second excitation source operating mode, wherein both the first and second excitation sources emit light onto the single location on the flow channel;
   a detector subsystem to that detects light emitted from the single location on the flow channel and generates a composite signal; and
   a processor coupled to the detector subsystem and adapted to separate the composite signal into composite mode signals each corresponding to a respective excitation source operating mode, wherein the processor is adapted to separate a composite mode signal into component mode signals corresponding to at least two overlapping emission spectra of fluorophores.

2. The system of claim 1, wherein the first excitation sources is a 488 nm laser and the second excitation source is selected from the group consisting of a 633 nm laser and a 375 nm laser.

3. The system of claim 1, wherein the excitation source operating modes are time division modulated.

4. The system of claim 3, wherein the processor demodulates the separated composite mode signals by deriving at least one additional component mode signal from the first composite mode signal corresponding to the first excitation source operating mode and the second composite mode signal corresponding to the second excitation source operating mode.

5. The system of claim 1, wherein the light subsystem further includes a third excitation source that emits light a third wavelength that is different from the first and second wavelengths; wherein the light subsystem further operates in at least one of the following excitation source operating modes:
   1) light emitted onto the single location on the flow channel from only the first excitation source and third excitation source;
   2) light emitted onto the single location on the flow channel from only the second excitation source and third excitation source; and
   3) light emitted onto the single location on the flow channel from the first excitation source, the second excitation source, and third excitation source.

6. The system of claim 5, wherein the first excitation sources is a 488 nm laser, the second excitation source is a 633 nm laser, and the third excitation source is a 375 nm laser.

7. The system of claim 5, wherein the light subsystem modulates between the excitation source operating modes.

8. The system of claim 7, wherein the excitation source operating modes are time division modulated.

9. The system of claim 8, wherein the processor demodulates the separated composite mode signals by deriving at least one additional component mode signal from at least two of: the first composite mode signal corresponding to the first excitation source operating mode, and the second composite mode signal corresponding to the second excitation source operating mode, and the third composite mode signal corresponding to the third excitation source operating mode.

10. The system of claim 1, wherein the detector subsystem includes a plurality of detectors in a spatial arrangement around the single location on the flow channel.

11. The system of claim 1, wherein the detector subsystem includes at least one photomultiplier tube.

12. The system of claim 1, wherein the detection system includes a number of detectors that collectively detect a number of fluorophores greater than the number of detectors.

13. A method for capturing multi source excitations from a single location on a flow channel comprising the steps of:
   emitting light onto a single location on a flow channel, including emitting light from a first excitation source at a first wavelength and emitting light from a second excitation source at a second wavelength that is different from the first wavelength, wherein the step of emitting light includes modulating between the following excitation source operating modes:
      in a first excitation source operating mode, emitting light onto the single location on the flow channel from only one of the first and second excitation sources; and
      in a second excitation source operating mode, emitting light onto the single location on the flow channel from both the first and second excitation sources;
   detecting light emitted from the single location on the flow channel and generating a composite signal;
   separating the composite signal into two or more composite mode signals, wherein each composite mode signal corresponds to a respective excitation source operating mode, and
   separating one or more of the composite mode signals into component mode signals corresponding to at least two overlapping emission spectra of fluorophores.

14. The method of claim 13, wherein the step of separating the composite mode signal into component mode signals includes demodulating the separated composite mode signals by deriving at least one component mode signal from the first composite mode signal corresponding to the first excitation source operating mode and the second composite mode signal corresponding to the second excitation source operating mode.

15. The method of claim 14, wherein the step of deriving at least one component mode signal from the first composite mode signal of the first excitation source operating mode and the second composite mode signal of the second excitation source operating mode, further includes the step selected from the group consisting of: subtracting, separating, filtering or distinguishing the first composite mode signal and the second composite mode signal.

16. The method of claim 13, wherein the step of emitting light includes emitting light from a third excitation source at a third wavelength that is different from the first and second wavelengths; wherein the step of emitting light includes further operating in at least one of the following excitation source operating modes:
   1) emitting onto the single location on the flow channel from only the first excitation source and third excitation source;
   2) emitting onto the single location on the flow channel from only the second excitation source and third excitation source; and
   3) emitting onto the single location on the flow channel from the first excitation source, the second excitation source, and third excitation source;
wherein the excitation source operating modes are modulated.

17. The method of claim 16, wherein the step of separating the composite mode signal into component mode signals includes demodulating the separated composite mode signals by deriving at least one component mode signal from at least two of: the first composite mode signal corresponding to the first excitation source operating mode, and the second composite mode signal corresponding to the second excitation source operating mode, and the third composite mode signal corresponding to the third excitation source operating mode.

18. The method of claim 17, wherein the step of deriving at least one component mode signal from at least two of the first composite mode signal, the second composite mode signal, and the third composite mode signal further includes the step selected from the group consisting of: subtracting, separating, filtering or distinguishing between at least two of the first composite mode signal, the second composite mode signal, and the third composite mode signal.

* * * * *

UNITED STATES PATENT AND TRADEMARK OFFICE
CERTIFICATE OF CORRECTION

| | | |
|---|---|---|
| PATENT NO. | : 8,077,310 B2 | Page 1 of 1 |
| APPLICATION NO. | : 11/848229 | |
| DATED | : December 13, 2011 | |
| INVENTOR(S) | : David C. Olson et al. | |

It is certified that error appears in the above-identified patent and that said Letters Patent is hereby corrected as shown below:

In column 6, line 14, "subsystem to that" should read --subsystem that--
In column 8, line 29, "mode, and the" should read --mode, the--

Signed and Sealed this
Fourteenth Day of February, 2012

David J. Kappos
*Director of the United States Patent and Trademark Office*